United States Patent [19]

Williams

[11] 4,001,944
[45] Jan. 11, 1977

[54] FREEZE-DRYING PROCESS
[75] Inventor: David C. Williams, Royal Oak, Mich.
[73] Assignee: Parke, Davis & Company, Detroit, Mich.
[22] Filed: Aug. 25, 1975
[21] Appl. No.: 607,306
[52] U.S. Cl. ............................... 34/5; 34/92; 165/185
[51] Int. Cl.² ............................... F26B 5/06
[58] Field of Search .................. 34/5, 92; 165/185
[56] References Cited
UNITED STATES PATENTS

| | | |
|---|---|---|
| 2,199,817 | 5/1940 | Flosdorf .................. 34/5 |
| 2,803,888 | 8/1957 | Cerletti .................. 34/92 |
| 3,009,258 | 11/1961 | Taylor .................... 34/92 |
| 3,391,466 | 7/1968 | Browwer et al. ......... 34/92 |
| 3,607,858 | 9/1971 | Querry et al. ........... 34/5 |

Primary Examiner—John J. Camby
Attorney, Agent, or Firm—David B. Ehrlinger; George M. Richards; Stephen Raines

[57] ABSTRACT

A process is provided for freeze-drying an aqueous liquid product which comprises distributing the liquid product in containers closely fitted in cavities of a tray-shaped heat-conducting solid metal block having relatively high heat transfer, subjecting the block to accelerated cooling such that the liquid in each container is frozen thereby freezing the liquid in each container at substantially the same rate, and drying the frozen product under vacuum while in the block so that the frozen product in each container is dried at substantially the same rate.

6 Claims, 3 Drawing Figures

FREEZE-DRYING PROCESS

SUMMARY AND DETAILED DESCRIPTION

This invention relates to a freeze-drying process. More particularly, the invention relates to an improved process for freeze-drying a liquid product by exposing the same in containers within a tray-shaped block of heat-conducting metal to cooling sufficient to freeze the liquid in a short period and drying the frozen product under vacuum.

In the prior art the conventional procedures for freeze-drying aqueous products, particularly pharmaceutical and biological products containing heat labile components, have required freezing the same at a slow rate in a relatively small volume and when drying the frozen product under vacuum by sublimation (lyophilization), also at a slow rate. The prior art method for freeze-drying or lyophilization is described, for example, in Remington's Pharmaceutical Science, 14th Edition, pages 1540–1542 (1970), Mack Publishing Company, Easton, Pennsylvania. The method uses a vacuum chamber and a condenser. The aqueous product contained in bottles is frozen in an inert atmosphere at a temperature below its eutectic temperature; the bottles are supported on a refrigerated shelf in the chamber. The chamber is evacuated usually below 0.1 Torr (100 microns of mercury pressure). The ice which is produced is then sublimed from the product onto the condenser at a temperature below that of the product. Finally, heat is introduced to the product by warming the shelf to provide energy for sublimation while keeping the product below its eutectic temperature. One difficulty with the prior art method is that the amount of liquid processed is necessarily low, for example, from 5–10 ml. per vial or bottle. Also, the method has required excessively long freezing periods, usually substantially more than one hour. It is found, for example, that slow freezing of certain products results in a poorly crystallized freeze-dried material which is difficult to redissolve. Thus, for parenteral administration of the product reconstitution with water may require an hour or more and is impractical, particularly in a case where delay of medication is contraindicated. Also, the prior art method of drying has been slow requiring, for example, as long as six days or more.

It is therefore an object of the present invention to provide a freeze-drying process which can be carried out in relatively short periods.

It is also an object of the invention to provide a process for the quick freezing and/or drying of aqueous products, pharmaceutical products, biologicals, blood products and the like.

It is a further object of the invention to provide freeze-dried products which can be readily redissolved.

It is a still further object to provide uniform freezing and freeze-drying for all containers or vials in the batch in order to minimize product variation from vial to vial with respect to uniformity, solubility, unitage and appearance.

These and other objects, advantages and purposes of the invention will be seen from the following description and the accompanying drawing illustrating a preferred embodiment of an apparatus for carrying out freeze-drying in which.

Figure 1:
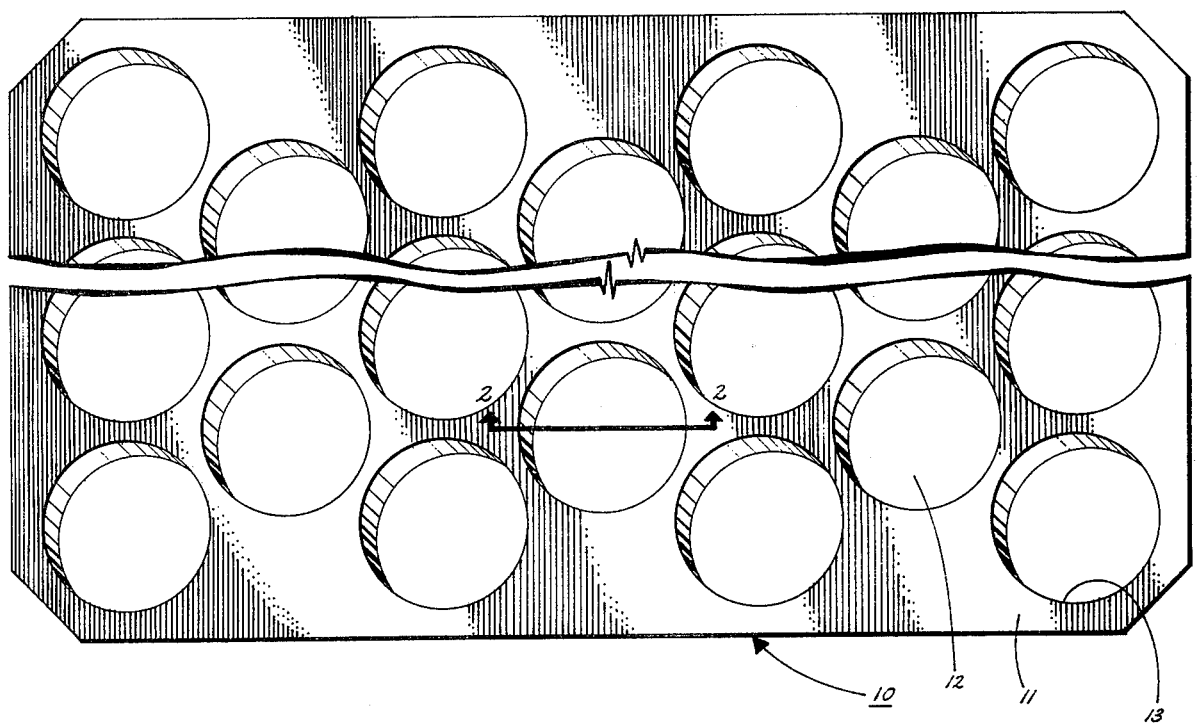
FIG. 1 is a top view of a freeze dryer tray according to the invention.

Referring to the drawing, the tray or block 10 adapted for use in a lyophilization chamber is generally rectilinear, flat on its top 11, and includes a number of cavities 12 having cylindrical sides 13. The tray is made of a heat-conducting metal or alloy being preferably fabricated from a single solid block of metal. Aluminum and magnesium are preferred metals. Cast aluminum is particularly satisfactory. Each cavity is dimensioned to receive a cylindrically-shaped lyophilization bottle 14 in a close fit. The bottle in turn has a stopper 15 of conventional design provided with an access opening for evacuation purposes and is adapted to be vacuum sealed into the throat of the bottle under compression. As shown the cavity 12 is flat at the bottom and the sides 13 are in close proximity to the bottom from the bottom to the top 11 so that voids within the bottle-filled cavity are minimized. Also, the top of the block is approximately even with the shoulder of the bottle so that the liquid fill line 16 is below the tray top 11. In other words, the liquid in the bottle filled to the fill line 16 is substantially confined (or physically located) within the body of the block. When the cavities of the block are filled with containers each containing liquid to the fill line 16, the liquid thus distributed is confined within the body of the block and the containers are mutually and evenly spaced by the body of the block. After the liquid is frozen and as the frozen product is being dried, the surface 17 where drying of the product is occurring (the drying boundary) moves progressively lower in the bottle until the water vapor is removed.

The present invention in freeze-drying an aqueous liquid product using a block tray of the type described comprises the steps of distributing the liquid within containers in cavities of the tray whereby for heat transfer the body of liquid in each container is substantially confined within the block and the containers are supported in a close fit and are mutually spaced by the body of the block, subjecting the block to cooling to freeze the liquid in a short period, less than about one hour, thereby freezing the liquid in each container at substantially the same rate and drying the frozen product under vacuum while within the block so that the frozen product in each container is dried at substantially the same rate.

It is found that the present process which is faster than prior art methods typically provides a superior dried product, particularly with respect to uniformity, solubility, unitage and appearance. The frozen product also has a desired (small) crystal form which dries more readily; the freeze-dried product redissolves promptly. For illustrative purposes, the invention will be described herein as it applies specifically to the freeze-drying of blood products or more specifically cryo-precipitated products such as anti-hemophilic factor in aqueous solution. In this process, the aqueous solution containing anti-hemophilic factor (obtained by a suitable procedure such as that described by Hershgold et al., J. Lab. & Clin. Med. 67:23, 1966) is first filled into bottles to the fill line 16, for convenience, bottles having a capacity of 40 ml. at the fill line. A solid cast aluminum tray 10 weighing 10 pounds is used having the array of cavities 12 illustrated in FIG. 1, 39 in number, each 1¾ inches in diameter. The tray measures 12

Figure 2:
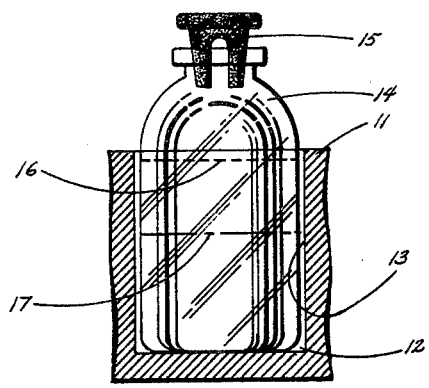
FIG. 2 is a side view of a lyophilization bottle located in a cavity of the tray cut away on line 2—2 of FIG. 1.
Figure 3:
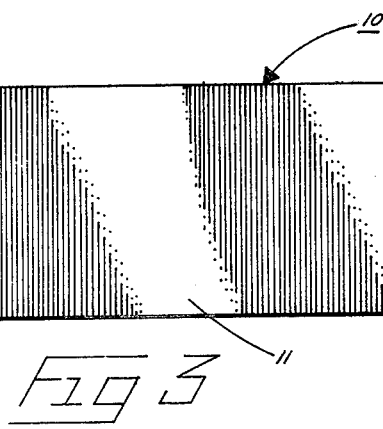
FIG. 3 is a side view of the tray.

× 12 × 2¼ inches. A preferred procedure is to pipet the solution at ambient temperature directly into the trayed bottles under sterile conditions. For freezing, the tray loaded with open stoppered bottles (as in FIG. 2) is placed into a freezer chest on a screen shelf or sparger which in turn is in direct contact with a bath of liquid nitrogen. The gaseous atmosphere in the chest is nitrogen so that oxygen contained in the bottles is displaced. The chest temperatures range between about −320° to −220° F. Cooling is continued until the liquid is frozen, usually about 45 minutes or less. If desired, the frozen product can be kept in the chest for longer periods without loss of quality. The frozen trayed product is then placed in a vacuum freeze-drying chamber and held under vacuum (50 microns) until dry, usually less than about 4½ days. The resulting freeze-dried product is completely satisfactory, particularly with respect to uniformity, appearance, stability, AHF content and reconstitution characteristics. For its end use, the dried material can be redissolved with physiological saline to a volume of 6 ml. in a short period, normally within 2 to 5 minutes, to provide a clear sediment-free liquid suitable for immediate parenteral administration. By contrast, AHF products produced by the prior art method (involving freezing longer than one hour and drying for about 6 days) usually require substantially longer periods, and often an hour or more, for reconstitution to a reasonable volume, i.e., 6 ml. or more.

While the invention in freeze-drying process has been described in considerable detail, it will be realized that wide variation in such detail can be made by those skilled in the art without departing from the spirit of the invention as hereinafter claimed.

I claim:

1. The process of freeze-drying parenteral aqueous liquid by means of a tray-shaped unitary block of heat-conducting metal having a plurality of spaced cavities therein each adapted to receive a container supported in a close fit so that the spacing between the containers is occupied substantially only by the heat-conducting metal, comprising the steps of
   distributing said liquid within containers in cavities of the block to a depth such that for heat transfer the body of liquid in each container is substantially confined within the block,
   subjecting the block to nitrogen bath cooling to freeze the liquid in a short period less than about one hour, thereby freezing the liquid in each container at substantially the same rate,
   and drying the frozen product under vacuum while confined within the block so that the frozen product in each container is dried in less than about 4½ days at substantially the same rate.

2. The process according to claim 1 where the heat-conducting metal is aluminum.

3. The process according to claim 1 where cooling is carried out in a zone maintained at temperatures in the range from about −320° to −220° F.

4. The process according to claim 1 where the aqueous liquid is a biological product.

5. The process according to claim 1 where the aqueous liquid is a blood product.

6. The process according to claim 1 where the aqueous liquid contains anti-hemophilic factor.

* * * * *